United States Patent [19]

Walker

[11] 4,435,407
[45] Mar. 6, 1984

[54] CERTAIN SUBSTITUTED β-OXO-α-CARBAMOYLPYRROLEPROPIONITRILES

[75] Inventor: Gordon N. Walker, Morristown, N.J.

[73] Assignee: Ciba-Geigy Corporation, Ardsley, N.Y.

[21] Appl. No.: 337,897

[22] Filed: Jan. 7, 1982

[51] Int. Cl.³ .................. C07D 401/12; A61K 31/44
[52] U.S. Cl. .................................... 424/263; 546/281; 546/143; 546/159; 548/195; 548/222; 548/251; 544/238; 544/324; 544/405
[58] Field of Search ...................... 546/281; 548/518; 424/263, 274

[56] References Cited
U.S. PATENT DOCUMENTS 4,061,767 12/1977 Ertel et al. ......................... 424/282
4,256,759 3/1981 Walker ............................... 424/274

FOREIGN PATENT DOCUMENTS 21207 12/1980 European Pat. Off. .

OTHER PUBLICATIONS

J. Am. Chem. Society 35 959 (1913).
Chem. Abstracts 74, 12358g (1971).

*Primary Examiner*—Alan L. Rotman
*Attorney, Agent, or Firm*—Norbert Gruenfeld

[57] ABSTRACT

β-Oxo-α-(heterocyclic substituted carbamoyl)-β-pyrrolyl-propionitriles are antiinflammatory and/or antiarthritic agents with immunomodulating properties. Their synthesis, pharmaceutical compositions thereof, and methods of treatment utilizing such compounds are included.

8 Claims, No Drawings

CERTAIN SUBSTITUTED β-OXO-α-CARBAMOYLPYRROLEPROPIONITRILES

BACKGROUND OF THE INVENTION

The inventor's U.S. Pat. No. 4,256,759, equivalent to European patent application No. 21,207 published Jan. 7, 1981, is directed to the antiinflammatory and antiarthritic β-oxo-α-(optionally substituted phenylcarbamoyl) pyrrolepropionitriles. The prior published literature disclosed anilides of α-acetylcyanoacetic acid described in U.S. Pat. No. 4,061,767 and J. Am. Chem. Soc. 35, 959 (1913), as well as anilides of α-benzoylcyanoacetic acid as described in the last said reference.

SUMMARY OF THE INVENTION

The present invention is concerned with α-(heterocyclic substituted carbamoyl)pyrrolepropionitriles of formula I below representing novel antiinflammatory, antirheumatic agents also having immunomodulating properties indicative of potential disease modifying effects.

The foregoing attributes render the carbamoylpyrrolepropionitriles of this invention useful, when administered alone or in combination, to mammals, e.g. for the treatment of arthritic diseases.

In view of the biological activity of the said compounds that is indicative of their ability to restore depressed cellular mediated immunity, the compounds of this invention may also be useful for the treatment of systemic lupus erythematosus, multiple sclerosis, carcinoma and the like where a defect of the said immune response is suspected.

DETAILED DISCLOSURE OF THE INVENTION

The invention relates to the novel β-oxo-α-(heterocyclic substituted carbamoyl)pyrrolepropionitriles of formula I useful as antirheumatic agents, processes for preparing same, pharmaceutical compositions comprising said compounds, and methods of treating rheumatic and arthritic diseases, e.g. rheumatoid arthritis and osteoarthritis by administration of said compounds and compositions to mammals.

Particularly the invention relates to compounds of the formula I or tautomers thereof

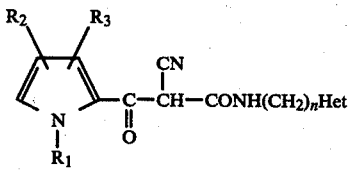
(I)

wherein $R_1$, $R_2$ and $R_3$ independently represent hydrogen or lower alkyl; n represents 0 or 1; Het represents a heterocyclic radical selected from the group consisting of pyridyl, thiazolyl, pyrrolyl, pyrimidinyl, pyrazinyl, thiadiazolyl, pyridazinyl, oxazolyl, isoxazolyl, imidazolyl, pyrazolyl, triazolyl, tetrazolyl, 4,5-dihydrothiazolyl, quinolyl, isoquinolyl, benzimidazolyl, benzothiazolyl or benzoxazolyl, said Het radicals being unsubstituted or mono- or disubstituted by lower alkyl, lower alkoxy, halogen, hydroxy or trifluoromethyl; pharmaceutically acceptable salts thereof; the lower alkyl enol ethers thereof; or the lower alkanoyl enol esters thereof.

Preferred embodiments of this invention relate to compounds of formula I or tautomers thereof wherein $R_1$ is hydrogen, lower alkyl; $R_2$ and $R_3$ represent hydrogen; n is 0 or 1; Het represents pyridyl, thiazolyl, pyrimidinyl, pyrazinyl, thiadiazolyl, pyridazinyl, oxazolyl, isoxazolyl, pyrazolyl, triazolyl, tetrazolyl, 4,5-dihydrothiazolyl, quinolyl, isoquinolyl, benzothiazolyl or benzoxazolyl, said Het radicals being unsubstituted or mono- or disubstituted by lower alkyl, lower alkoxy or halogen; or pharmaceutically acceptable salts thereof.

Further preferred are said compounds of formula I, or tautomers thereof, wherein $R_1$ is hydrogen, methyl, ethyl, propyl or butyl; $R_2$ and $R_3$ are hydrogen; n is 0 or 1; and Het represents last said heterocyclic radicals unsubstituted or mono- or disubstituted by methyl, ethyl, methoxy or chloro.

Especially preferred are compounds of formula I, or tautomers thereof, wherein $R_1$ is lower alkyl; $R_2$ and $R_3$ are hydrogen; n is 0; and Het represents 2-pyridyl, 2-thiazolyl, 2-pyrazinyl, 3-pyridazinyl or 2-benzothiazolyl, said Het radicals being unsubstituted or mono- or disubstituted by lower alkyl, lower alkoxy or halogen; or pharmaceutically acceptable salts thereof.

Particularly preferred are compounds of formula I wherein $R_1$ is methyl; $R_2$ and $R_3$ are hydrogen; n is 0; Het represents 2-pyridyl, 2-thiazolyl, 2-pyrazinyl or 3-pyridazinyl, said Het radical being unsubstituted or monosubstituted by methyl, methoxy or chloro; or pharmaceutically acceptable salts thereof.

The general definitions used herein have the following meaning within the scope of the present invention.

The term "lower" referred to above and hereinafter in connection with organic radicals or compounds respectively defines such with up to and including 7, preferably up and including 4 and advantageously one or two carbon atoms.

A lower alkyl group preferably contains 1–4 carbon atoms and represents for example ethyl, propyl, butyl or advantageously methyl.

A lower alkoxy group preferably contains 1–4 carbon atoms and represents for example ethoxy, propoxy, isopropoxy or advantageously methoxy.

Halogen preferably represents chlorine, but may also be bromine, fluorine or iodine.

Lower alkanoyl represents preferably acetyl or propionyl.

A heterocyclic radical represents a monocyclic or bicyclic heterocyclic aromatic or said partially hydrogenated radical optionally substituted by lower alkyl, lower alkoxy, halogen, hydroxy or trifluoromethyl.

Tautomers of the compounds of formula I may be represented by the corresponding enol structure of formula Ia

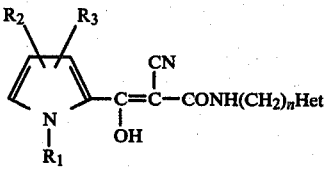
(Ia)

wherein $R_1$, $R_2$, $R_3$, n, and Het have meaning as defined in formula I.

The compounds of formula I have acidic properties and form as derivatives of the enolic tautomeric structure of formula Ia said lower alkyl enol ethers, alkanoyl enol esters, or salts thereof with pharmaceutically acceptable bases, such as alkali metal, alkaline earth metal, copper or zinc hydroxides; ammonia, mono-, di- or tri-lower (alkyl or hydroxyalkyl)amines, monocyclic amines or alkylenediamines, e.g. sodium, potassium, magnesium, ammonium, mono-, di- or tri-(methyl, ethyl or hydroxyethyl)-ammonium, pyrrolidinium, ethylenediammonium or morpholinium salts; or various hydrates thereof.

Said compounds of formula I, wherein said Het radical is basic in nature, also form acid addition salts, which are preferably such of therapeutically acceptable inorganic or organic acids, such as strong mineral acids, for example hydrohalic e.g. hydrochloric or hydrobromic acid; sulfuric, phosphoric, nitric or perchloric acid; aliphatic or aromatic carboxylic or sulfonic acids e.g. formic, acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicyclic, pamoic, nicotinic, methanesulfonic, ethanesulfonic, hydroxyethanesulfonic, benzenesulfonic, p-toluenesulfonic, naphthalenesulfonic, sulfanilic or cyclohexylsulfamic acid.

The compounds of the invention exhibit valuable pharmacological properties, primarily antiinflammatory, antirheumatic, immunopotentiating and antiarthritic activity. These can be demonstrated by in-vitro or in-vivo tests, using for the latter advantageously mammals, such as rats, guinea pigs or dogs, as test objects. The compounds of the invention can be administered to the animals either enterally, preferably orally, parenterally, e.g. subcutaneously or intravenously, or topically, for example, in the form of aqueous or oily solutions or starchy suspensions. The applied dosage may range between about 0.1 and 100 mg/kg/day, preferably between about 1 and 50 mg/kg/day. The tests chosen are among the classical assay methods for said activities, such as the carrageenin paw-edema, or adjuvant arthritis test in rats, the canine synovitis or ultraviolet erythema assays, or more recent tests, such as neutral protease inhibition, described in Arthritis Rheum. 17, 47 (1974), or inhibition of leukocyte chemotaxis, described in Ann. N.Y. Acad. Sci., 256, 177 (1975); or decrease of neutrophil adherence, described in Amer. J. Med. 61, 597 (1976); or inhibition of prostaglandin synthetase, described in Biochem. 10, 2372 (1971).

Immunopotentiating effects are determined in BCG-immunized animals in vitro and in vivo.

Enhancement of cell-mediated immunity is determined in vitro as follows by measurement of increased chemotaxis of monocytes.

Male Charles River rats, weighing 250–300 g are immunized by intradermal injections of 0.1 ml Bacillus Calmette Guerin (BCG) vaccine. One week later, the animals are injected with 10 ml of a sterile 2% rice starch solution intraperitoneally, to induce the accumulation of macrophages. On day 11 after immunization, the animals are sacrificed and peritoneal macrophages collected with 20 ml of Gey's balanced salt solution containing heparin (25 units/ml). The harvested cells are centrifuged at 1000 RPM for 10 minutes, washed with 50 ml more of Gey's solution at the same speed and time, and then they are resuspended in Gey's solution containing 0.1% human serum albumin (Fraction V, Sigma Co. pH=7.1) to yield a concentration of $2 \times 10^6$ cells/ml.

The test substances are dissolved in dimethylacetamide to yield a $1 \times 10^{-2}$ M solution. Subsequent dilutions are made with Gey's solution, and they are finally added to the above cell suspension to yield the appropriate final concentrations of $10^{-4}$, $10^{-5}$, $10^{-6}$ and $10^{-7}$ M. Said substances remain with the cells after the suspensions are distributed over the upper compartment of the modified Boyden chemotaxis chambers.

E. coli lipopolysaccharide (Difco) activated rat serum (1/10 dilution at pH=7.1) is used as the chemotactic agent and placed in the lower compartment of said chambers. The cell compartment of the chamber is separated from the chemotactic solution by a 8 micron pore size cellulose filter membrane, the chambers are set up in triplicate and incubated for 5 hours at 37° C. Cell suspensions alone, without test compound, serve as controls for cell-migration. After incubation, the filters are removed, fixed and stained with Weigert's iron hematoxylin, and four fields of the lowermost surface of the filter are examined microscopically at a magnification of 320. The average of the number of neutrophils counted in those four fields is used as an index of chemotactic activity.

The enhancement of cell-mediated immunity is determined in vivo in the BCG-immunized arthritic rat by measurement of delayed hypersensitivity reaction essentially as described in Current Therapeutic Research 30, S34 (1981).

Charles River male rats weighing 325–400 g are sensitized by intradermal injection into the right hind foot pad with 250 μg per animal of Mycobacterium tuberculosis (Difco) emulsified in Freund's incomplete adjuvant. Animals are immunized with 0.1 ml of BCG vaccine intradermally on day 18 after adjuvant injection. Corn starch suspensions of drugs are administered orally. Control animals are dosed with cornstarch vehicle only. All animals are skin-tested with 10 μg PPD intradermally on day 29 to elicit skin reactions. The diameter of the erythema and induration reaction is measured 24 hours after antigen challenge. An increase in the diameter of the erythema is indicative of enhanced cellular immunity.

The carrageenin paw-edema assay for antiinflammatory activity is carried out in rats as follows:

One hour after compounds are administered orally, 0.1 ml of carrageenin (1%) is injected into plantar area of one hind paw. Difference of swelling is measured between contralateral and injected paw by means of mercury displacement at designated times.

The established adjuvant arthritis test for antiarthritic activity is performed essentially as described in Proc. Soc. Biol. Med. 137, 506 (1971).

Illustrative of the invention, β-oxo-α-(2-pyridylcarbamoyl)-β-(1-methyl-2-pyrroyl)propionitrile of example 1 and β-oxo-α-(2-thiazolylcarbamoyl)-β-(1-methyl-2-pyrrolyl)propionitrile of example 2 both at a dose of 100 mg/kg/p.o. afford protection against carrageenin-induced edema in rats measured 3 hours after administration by 51% and 38% respectively.

Furthermore the said compound of example 1 is active in the established adjuvant arthritis test in the rat at a dose of 25 mg/kg/p.o. (29% protection).

Indicative of the immunopotentiating activity of the compounds of this invention, said compound of example 2 exhibits significant activity in the skin test in the BCG-immunized adjuvant arthritic rat at a dose of 25 mg/kg/p.o.

The aforementioned advantageous properties render the compound of the invention useful as antiinflammatory, antiarthritic, and immunopotentiating agents especially for the treatment and amelioration of e.g. inflammatory disorders, such as rheumatoid arthritis and osteoarthritis in mammals, including man.

The compounds of the invention are preferably prepared according to the following method:

(1) condensing a compound of formula II, or

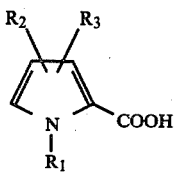

a reactive functional derivative thereof, with a compound of formula III $$N \equiv CCH_2CONH(CH_2)_n Het \qquad (III)$$

wherein $R_1$, $R_2$, $R_3$, n and Het have meaning as previously defined; and (2) optionally converting a resulting compound of formula I to another compound of formula I.

When the starting material is a reactive functional derivative of a compound of formula II, said condensation is advantageously performed in the presence of metallizing agents such as alkali metals, metal alkoxides or hydrides, e.g. sodium hydride, potassium t-butoxide, thallous ethoxide, or under phase transfer conditions, in polar solvents e.g. 1,2-dimethoxyethane, dimethylformamide, at temperatures ranging from about 0° to 100°, preferably at 25° to 50°.

Reactive functional derivatives of the carboxylic acids of formula II are for example anhydrides especially mixed anhydrides, acid halides, the acid azide, and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters.

The condensation of a free carboxylic acid of formula II with a compound of formula III may be carried out in the presence of a condensing agent, e.g. diethyl phosphorocyanidate, in the presence of a base, e.g. triethylamine, in an inert polar solvent, e.g. dimethylformamide.

Intermediates of formula III are conveniently prepared from cyanoacetic acid and $Het(CH_2)_n NH_2$ in the presence of condensing agents such as dicyclohexylcarbodiimide, 1,1'-carbonyldiimidazole and the like, according to standard procedures known to the art and exemplified herein.

The compounds of the invention may also be prepared according to the following methods:

(a) condensing together the compounds of the formulae

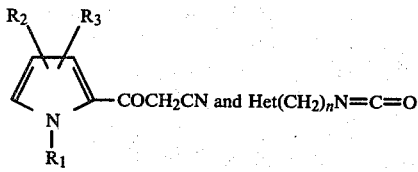

The addition of the isocyanate to the propionitrile (U.S. Pat. No. 4,256,759) may be carried out according to said U.S. patent i.e., in the absence or presence of an inorganic or organic base, such as sodium hydride, or in the presence or absence of a polar solvent, such as an ether, e.g. diethyl ether or tetrahydrofuran, and/or an amide or sulfoxide, e.g. dimethylformamide or -sulfoxide; advantageously at elevated temperatures, e.g. at about 150° if no base is used.

The isocyanates may be prepared from the corresponding heterocyclic acid azides by the well-known Curtius rearrangement.

(b) condensing together the compounds of the formulae

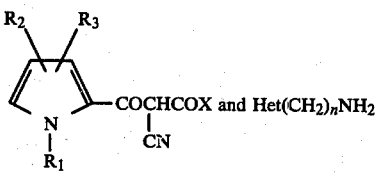

wherein $R_1$, $R_2$, $R_3$, n and Het are as defined above, X is lower alkoxy, lower alkanoyloxy or halogen.

The preparation of the starting material and the condensation is carried out according to U.S. Pat. No. 4,256,759 advantageously between room temperature and about 150°, either with equivalent amounts of the reactants, preferably when the ester is used, or with an excess of the amine, or in the presence of another base, such as a tertiary amine, e.g. a tri-lower alkyl-amine or pyridine, when the halide or anhydride is used, in order to neutralize the generated acid. The lower alkanol, generated in the reaction with said esters, is preferably distilled off together with diluent, such as an aromatic hydrocarbon, e.g. benzene, toluene or xylene.

(c) ring opening a compound of the formula,

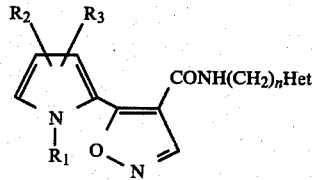

with a strong base.

The ring opening reaction, a reaction known to the art as described in J. Am. Chem. Soc. 35, 959 (1913), is carried out in the presence of said strong inorganic or organic bases, e.g. alkali metal hydroxides or tri-lower alkyl-aralkylammonium hydroxides, e.g. trimethylbenzylammonium hydroxide.

The compounds of Formula I, so obtained, can be converted into each other according to methods known per se. Thus, for example, resulting enols can be etherified, e.g. with lower diazoalkanes, or esterified, e.g. with lower alkanoic acid anhydrides; or converted into salts with said pharmaceutically acceptable acids and bases, e.g. an aqueous alkali metal hydroxide or a hydrohalic acid, advantageously in the presence of an ethereal or alcoholic solvent respectively, such as a lower alkanol. From the solutions of the latter, the salts may be precipitated with said ethers, e.g. diethyl ether or tetrahydrofuran, at moderate temperatures, e.g. below 100°. Resulting salts may be converted into the free compounds by treatment with acids or bases as mentioned above. These or other salts, for example, the picrates, can also be used for purification of the compounds obtained. In view of the close relationship between the free compounds and the compounds in the form of their salts, whenever a compound is referred to in this context, a corresponding salt is also intended provided such is possible or appropriate.

The starting materials used are known, or if new, can be prepared according to the methods used in the references cited under "Background of the Invention" or illustrated by the examples herein.

The above reactions are otherwise carried out according to standard methods, in the presence or absence of diluents, preferably such as are inert to the reagents and are solvents thereof, of catalysts, condensing or neutralization agents and/or inert atmospheres, at low temperatures, room temperature or elevated temperatures, at atmospheric or superatmospheric pressure.

The invention also comprises any modification of the above processes, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives, preferably alkali metal or trialkylammonium salts of said enols. In said processes of the invention those starting materials are advantageously selected, which yield the above-described preferred embodiments of the invention.

The invention also relates to novel intermediates and processes for their manufacture.

Depending on the choice of starting materials and methods, the new compounds may be in the form of one isomer or mixtures thereof, provided such isomers are possible.

The compounds, including their salts, can also be obtained in the form of their hydrates, or include other solvents used for the crystallization.

The pharmaceutical compositions according to the invention are those suitable for enteral, such as oral or rectal, and parenteral administration to mammals, including man, for the treatment of inflammatory, arthritic and immunologically mediated diseases such as osteoarthritis and rheumatoid arthritis comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions containing an effective amount thereof in conjunction or admixture with excipients suitable for either enteral, parental or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories or topical lotions are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

A unit dosage for a mammal of about 50 to 70 kg may contain between about 10 to 200 mg of the active ingredient.

The following examples are intended to illustrate the invention and are not to be construed as being limitations thereon. Temperatures throughout are given in degrees Centigrade and all parts wherever given are parts by weight. If not otherwise stated, evaporations are carried out under reduced pressure, preferably between about 15 and 100 mm Hg.

EXAMPLE 1

β-Oxo-α-(2-pyridylcarbamoyl)-β-(1-methyl-2-pyrrolyl)propionitrile

Sodium hydride (0.9 g; 50% mineral oil) was washed with petroleum ether by decantation and suspended in 10 ml of dimethylformamide. There was added 2.5 g of 2-(cyanoacetylamino)pyridine and 10 ml of 1,2-dimethoxyethane. When effervescence subsided, the suspension was treated (swirling) with a solution of the N-methyl-2-pyrroloyl chloride (prepared from 2.0 g of N-methylpyrrole-2-carboxylic acid as described below) in 10 ml of 1,2-dimethoxyethane. After the moderately exothermic reaction, the brown mixture was let stand at room temperature overnight. Water was added (ca. 150 ml) and the aqueous solution was washed with ethyl acetate and acidified with 3 ml of 6 N HCl. The product was collected, washed with water, air dried, and the crude material (m.p. 210°–211° dec.) recrystallized from dimethylformamide-methanol or from ethanol to give β-oxo-α-(2-pyridylcarbamoyl)-β-(1-methyl-2-pyrrolyl)propionitrile, m.p. 211°–212° dec., the compound of formula I, wherein $R_1$ is methyl, $R_2$ and $R_3$ are hydrogen, n is 0 and Het is 2-pyridyl.

The starting materials were prepared as follows:

Cyanoacetic acid (4.5 g) and 5.0 g of 2-aminopyridine, each in acetonitrile, were combined, and the suspension (150 ml) treated rapidly with a solution of 12.0 g of dicyclohexylcarbodiimide (DCCI) in 60 ml of acetonitrile. After stirring 4 hrs. and filtering, the filtrate was evaporated and the residue triturated with ether to give 2-(cyanoacetylamino)pyridine, m.p. 159°–161°. Recrystallization from ethyl acetate raised melting point to 162°–3°.

A solution of 2.5 g of N-methylpyrrole-2-carboxylic acid in 125 ml of dry ether and 2.2 g of anhydrous triethylamine was stirred and treated gradually with a solution of 2.5 g of thionyl chloride in 30 ml of dry ether. The suspension was stirred 1 hr, filtered, and the filtrate evaporated to a small volume, filtered again, and evaporated. The residual oil (crude acid chloride) was dissolved in 1,2-dimethoxyethane (glyme) and the solution used directly in the acylation step.

EXAMPLE 2

β-Oxo-α-(2-thiazolylcarbamoyl)-1-(1-methyl-2-pyrrolyl)propionitrile

To the suspension of 2.1 g of 50% NaH mineral oil (washed with petroleum ether) in 25 ml of 1,2-dimethoxyethane and 15 ml of dimethylformamide was added 6.7 g of 2-(cyanoacetylamino)thiazole. After the moderately exothermic, effervescent reaction of the hydride, there was added (swirling) a solution of N-methyl-2-pyrroloyl chloride (prepared from 2.5 g of the acid) in 20 ml of 1,2-dimethoxyethane. The dark suspension resulting from the exothermic reaction was let stand overnight. After treatment with ca. 300 ml water, the filtered aqueous solution was acidified with 6 ml of 6 N HCl. The crude product was collected, redissolved in NaHCO$_3$ solution, and the filtered solution carefully acidified with 6 N HCl. The product was collected, washed with water, dried, and triturated with methanol to give crystals, m.p. 201°–2° dec. Recrystallization from dimethylformamide-methanol gave β-oxo-α-(2-thiazolylcarbamoyl)-β-(1-methyl-2-pyrrolyl)propionitrile, m.p. 208°–9° dec.

The starting material was prepared as follows:

4.5 g of cyanoacetic acid and 5.3 g of 2-aminothiazole, each in acetonitrile were combined, and the suspension (60 ml) was treated with a solution of 12.0 g of dicyclohexylcarbodiimide in 30 ml of acetonitrile. After exothermic reaction (and solidification) additional acetonitrile (60 ml) was added and the mixture stirred 1 hr and let stand overnight. The collected solid (20 g) was stirred with dilute (ca. 2%) NaOH solution and filtered. The filtrate was acidified with 6 N HCl and the product collected, washed with water, dried (m.p. 229°–230°) and recrystallized from acetone to give 2-(cyanoacetylamino)thiazole, m.p. 231°–2° dec.

EXAMPLE 3

To the stirred suspension of 1.4 g of 50% sodium hydride (washed with petroleum ether) in 50 ml of 1,2-dimethoxyethane was added 5.4 g of 2-(cyanoacetylaminomethyl)-pyridine in portions, and when the sodium hydride was consumed there was added a solution of the N-methyl-2-pyrroloyl chloride prepared from 3.5 g of the acid in 20 ml of 1,2-dimethoxyethane. After the exothermic reaction, the yellow suspension was let stand overnight, then evaporated to smaller volume on steam cone, cooled, and treated with water (250 ml). The aqueous solution was washed with ethyl acetate, and the ethyl acetate layer was re-extracted with dilute NaHCO$_3$ solution. The aqueous solutions, on careful acidification with 6 N HCl gave material which was collected, washed with water, and dried to give crystals, m.p. 114°–115° dec. Recrystallization from ethanol yielded β-oxo-α-(2-pyridylmethylcarbamoyl)β-(1-methyl-2-pyrrolyl)propionitrile, m.p. 116°–118° dec., the compound of formula I wherein R$_1$=CH$_3$, R$_2$ and R$_3$=H, n=1, and Het=2-pyridyl.

The starting material was prepared as follows:

To a solution of 6.8 g of cyanoacetic acid in 200 ml of acetonitrile was added a solution of 8.65 g of 2-aminomethylpyridine in 50 ml of acetonitrile, and to the resulting suspension there was added rapidly (with stirring) a solution of 18.5 g of dicyclohexylcarbodiimide in 50 ml of acetonitrile. After stirring 5 hours and standing overnight, the suspension was filtered. The filtrate was evaporated, and the crude residue was triturated with ether-ethyl acetate to give crystals, m.p. 78°–80°. Recrystallization from toluene yielded the 2-(cyanoacetylaminomethyl)-pyridine, m.p. 81°–82°.

EXAMPLE 4

The following compounds of formula I, wherein R$_1$ is methyl, R$_2$ and R$_3$ are hydrogen, and n is 0, were prepared analogously to compounds of examples 1–3.

| No. | Het | m.p. | Solv. of recrystallization |
|---|---|---|---|
| 4/a | 2-pyrimidinyl | 207–8° dec. | DMF—MeOH |
| 4/b | 6-methyl-2-pyridyl | 200–1° dec. | DMF—MeOH |
| 4/c | 4-methyl-2-thiazolyl | 208–9° dec. | DMF—EtOAC |
| 4/d | 5-methyl-2-(1,3,4-thiadiazolyl) | 178–80° dec. | CH$_3$OH—EtOH |
| 4/e | 2-pyrazinyl | 169–71° dec. | EtOAc |
| 4/f | 5-methyl-3-isoxazolyl | 162–6° dec. | MeOH |
| 4/g | 4,5 dihydro-2-thiazolyl | 191–2° dec. | DMF—EtOH |
| 4/h | 6-methoxy-3-pyridazinyl | 178–80° dec. | DMF—EtOH |
| 4/i | 3-quinolyl | 212–3° dec. | DMF—EtOH |

The starting materials of formula III wherein n is 0, corresponding to the above compounds of formula I, were prepared, analogous to procedures given in Examples 1 to 3, from the corresponding heterocyclic amines.

| No. | Het | m.p. | Solv. of recrystallization |
|---|---|---|---|
| 4/a' | 2-pyrimidinyl | 186–7° dec. | MeOH |
| 4/b' | 6-methyl-2-pyridyl | 97–9° | ethyl ether |
| 4/c' | 4-methyl-2-thiazolyl | 176–7° | MeOH |
| 4/d' | 5-methyl-2-(1,3,4-thiadiazolyl) | 250–1° dec. | DMF—EtOH |
| 4/e' | 2-pyrazinyl | 216–7° dec. | MeOH—EtOH |
| 4/f' | 5-methyl-3-isoxazolyl | 227–8° | MeOH |
| 4/g' | 4,5-dihydro-2-thiazolyl | 139–40° dec. | MeOH—EtOAc |
| 4/h' | 6-methoxy-3-pyridazinyl | 212–4° dec. | DMF—MeOH |
| 4/i' | 3-quinolyl | 214–6° | EtOH |

EXAMPLE 5

By methods analogous to those described in Examples 1 to 3, the following compounds of formula I wherein n=o are prepared:

| No. | R$_1$ | R$_2$ | R$_3$ | Het |
|---|---|---|---|---|
| 5/a | ethyl | H | H | 2-pyridyl |
| 5/b | isobutyl | H | H | 2-thiazolyl |
| 5/c | CH$_3$ | 3-methyl | 5-methyl | 6-methyl-2-pyridyl |
| 5/d | CH$_3$ | H | H | 2-benzothiazolyl |
| 5/e | CH$_3$ | H | H | 5-chloro-2-benzoxazolyl |
| 5/f | CH$_3$ | H | H | 5-chloro-2-pyridyl |

The variously lower alkyl substituted pyrrole-2-carboxylic acids of formula II are conveniently prepared by hydrolysis of the corresponding esters described in U.S. Pat. No. 4,256,759.

EXAMPLE 6

By treatment of β-Oxo-α-(2-pyridylcarbamoyl)-β-(1-methyl-2-pyrrolyl)propionitrile with an equivalent amount of a concentrated aqueous or alcoholic solution of sodium, potassium or calcium hydroxide or ethoxide and evaporating to dryness, the corresponding sodium, potassium or calcium salt of the compound of formula Ia, wherein $R_1=CH_3$, $R_2$ and $R_3=H$, $n=0$, and Het=2-pyridyl, is obtained.

EXAMPLE 7

By treatment of β-oxo-α-(2-pyridylcarbamoyl)-β-pyridylcarbamoyl)-β-(1-methyl-2-pyrrolyl)propionitrile in ethanol with an equivalent amount of ethanolic HCl, and evaporating the reaction mixture to dryness, β-oxo-α-(2-pyridylcarbamoyl)-β-(1-methyl-2-pyrrolyl)propionitrile hydrochloride is obtained.

EXAMPLE 8

To the suspension of 12.9 g of 1-methyl-β-oxo-2-pyrrolepropionitrile (U.S. Pat. No. 4,256,759) in 150 ml of dry toluene and 10.1 g of anhydrous triethylamine are added 10.8 g of 3-pyridyl isocyanate while stirring. After all solids are dissolved, the solution is allowed to stand at room temperature overnight. The mixture is evaporated to dryness, the residue taken up in methanol and the solution is neutralized to pH ca. 6 with 3 N hydrochloric acid and diluted with 600 ml of water. The resulting precipitate is collected, washed with water, and dried to yield the β-oxo-α-(3-pyridylcarbamoyl)-β-(1-methyl-2-pyrrolyl)propionitrile.

EXAMPLE 9

To 500 ml of ethereal diazomethane, generated from 10.3 g of N-nitroso-N-methylurea with 35 ml of 45% aqueous potassium hydroxide and dried over such pellets, are added 3,9 g of β-oxo-α-(2-pyridylcarbamoyl)-β-(1-methyl-2-pyrrolyl)propionitrile are added. After the nitrogen evolution ceases, the solution is filtered and evaporated. The residue is purified to yield the corresponding methyl enol ether, i.e. the 1-methyl-β-methoxy-α-(2-pyridylcarbamoyl)-β-(1-methyl-2-pyrrolyl)acrylonitrile.

EXAMPLE 10

The mixture of 1.1 g of 1-methyl-β-oxo-α-ethoxycarbonyl-2-pyrrolepropionitrile (U.S. Pat. No. 4,256,759), 1.2 g of 3-aminopyridine and 60 ml of xylene, is refluxed for 4½ hours. After standing and cooling to room temperature overnight, the solution is filtered, evaporated and the residue is purified to yield β-oxo-α-(3-pyridylcarbamoyl)-β-(1-methyl-2-pyrrolyl)propionitrile.

EXAMPLE 11

Preparation of 1,000 capsules each containing 25 mg of the active ingredient:

| Formula: | |
|---|---|
| β-Oxo-α-(2-thiazolylcarbamoyl)-β-(1-methyl-2-pyrrolyl)propionitrile | 25.0 g |
| Lactose | 207.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 315 mg of said mixture each, using a capsule filling machine.

Analogously capsules are prepared, containing 25–100 mg of the other compounds disclosed and illustrated herein.

EXAMPLE 12

Preparation of 10,000 tablets each containing 100 mg of the active ingredient:

| Formula: | |
|---|---|
| β-Oxo-α-(2-pyridylcarbamoyl)-β-(1-methyl-2-pyrrolyl)propionitrile | 1,000.00 g |
| Lactose | 2,535,00 g |
| Corn starch | 125.00 g |
| Polyethylene glycol 6,000 | 150.00 g |
| Talcum powder | 150.00 g |
| Magnesium stearate | 40.00 g |
| Purified water | q.s |

Procedure

All the powders are passed through a screen with openings of 0.6 mm. Then, the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches with 10.3 mm diameter, uppers bisected.

Analogously tablets are prepared, containing 50–200 mg of one of the other compounds illustrated by the previous examples.

What is claimed is:

1. A compound of the formula

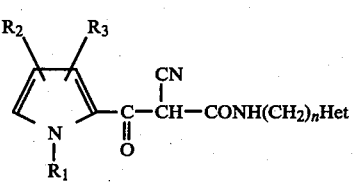

or a tautomer thereof wherein $R_1$, $R_2$ and $R_3$ independently represent hydrogen or lower alkyl; n represents 0 or 1; Het represents pyridyl, unsubstituted or mono or disubstituted by lower alkyl, lower alkoxy, halogen, hydroxy or trifluoromethyl; a pharmaceutically acceptable salt thereof.

2. A compound of claim 1 wherein $R_1$ is hydrogen or lower alkyl; $R_2$ and $R_3$ represent hydrogen; n is 0 or 1; Het represents pyridyl unsubstituted or mono- or disubstituted by lower alkyl, lower alkoxy or halogen; or a pharmaceutically acceptable salt thereof.

3. A compound of claim 1 wherein $R_1$ is lower alkyl; $R_2$ and $R_3$ are hydrogen; n is 0; and Het represents 2-pyridyl unsubstituted or mono- or disubstituted by lower alkyl, lower alkoxy or halogen; or a pharmaceutically acceptable salt thereof.

4. A compound of claim 3 wherein $R_1$ is methyl; $R_2$ and $R_3$ are hydrogen; n is 0; Het represents 2-pyridyl unsubstituted or monosubstituted by methyl, methoxy or choro; or a pharmaceutically acceptable salt thereof.

5. A compound of claim 3 being β-oxo-α-(2-pyridylcarbamoyl)-β-(1-methyl-2-pyrrolyl)propionitrile or a pharmaceutically acceptable salt thereof.

6. A compound of claim 2 wherein $R_1$ is hydrogen, methyl, ethyl, propyl or butyl; $R_2$ and $R_3$ are hydrogen; n is 0 or 1; Het represents pyridyl unsubstituted or mono- or disubstituted by methyl, ethyl, methoxy or chloro; or a pharmaceutically acceptable salt thereof.

7. An antiinflammatory and antiarthritic pharmaceutical composition comprising a correspondingly effective amount of a compound of claim 1 in combination with one or more pharmaceutically acceptable carriers.

8. A method of treating inflammatory and arthritic conditions in mammals which comprises administering to a mammal in need thereof an effective amount of a composition of claim 7.

* * * * *